US008187293B2

(12) United States Patent
Kirchhevel

(10) Patent No.: US 8,187,293 B2
(45) Date of Patent: May 29, 2012

(54) MICROSURGICAL INSTRUMENT

(75) Inventor: G. Lamar Kirchhevel, Laguna Niguel, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/348,118

(22) Filed: Feb. 6, 2006

(65) Prior Publication Data

US 2007/0185512 A1 Aug. 9, 2007

(51) Int. Cl.
*A61B 17/32* (2006.01)
(52) U.S. Cl. ........................................ 606/171; 606/180
(58) Field of Classification Search .................. 606/166, 606/167, 170, 171, 177, 180; 604/22
See application file for complete search history.

(56) References Cited

U.S. PATENT DOCUMENTS

| | | | |
|---|---|---|---|
| 3,884,238 A | 5/1975 | O'Malley et al. | |
| 4,493,698 A | 1/1985 | Wang et al. | |
| 4,577,629 A | 3/1986 | Martinez | |
| 4,696,298 A | 9/1987 | Higgins et al. | |
| 4,757,814 A | 7/1988 | Wang et al. | |
| 4,768,506 A | 9/1988 | Parker et al. | |
| 4,819,635 A | 4/1989 | Shapiro | |
| 4,841,984 A | 6/1989 | Armeniades et al. | |
| 4,909,249 A * | 3/1990 | Akkas et al. | 606/107 |
| 4,940,468 A | 7/1990 | Petillo | |
| 4,986,827 A | 1/1991 | Akkas et al. | |
| 5,019,035 A | 5/1991 | Missirlian et al. | |
| 5,020,535 A | 6/1991 | Parker et al. | |
| 5,024,652 A | 6/1991 | Dumenek et al. | |
| 5,047,008 A | 9/1991 | de Juan, Jr. et al. | |
| 5,059,204 A | 10/1991 | Lawson et al. | |
| 5,061,238 A | 10/1991 | Shuler | |
| 5,106,364 A * | 4/1992 | Hayafuji et al. | 604/22 |
| 5,176,628 A | 1/1993 | Charles et al. | |
| 5,226,910 A * | 7/1993 | Kajiyama et al. | 606/171 |
| 5,284,472 A | 2/1994 | Sussman et al. | |
| 5,354,268 A | 10/1994 | Peterson et al. | |
| 5,380,280 A | 1/1995 | Peterson | |
| 5,423,844 A | 6/1995 | Miller | |
| 5,474,532 A | 12/1995 | Steppe | |
| 5,520,652 A | 5/1996 | Peterson | |
| 5,630,827 A | 5/1997 | Vijfvinkel | |
| 5,674,194 A | 10/1997 | Jung et al. | |
| 5,733,297 A | 3/1998 | Wang | |
| 5,782,849 A | 7/1998 | Miller | |
| 5,792,166 A | 8/1998 | Gordon et al. | |
| 5,833,643 A | 11/1998 | Ross et al. | |
| 6,010,496 A | 1/2000 | Appelbaum et al. | |
| 6,383,203 B1 | 5/2002 | Makihara | |
| 6,488,695 B1 | 12/2002 | Hickingbotham | |
| 6,514,268 B2 * | 2/2003 | Finlay et al. | 606/170 |
| 6,773,445 B2 | 8/2004 | Finlay et al. | |
| 2002/0161398 A1 | 10/2002 | Hickingbotham | |

OTHER PUBLICATIONS

Hiroshi, et al, "Operating Cutter", Published JP03039158, Feb. 20, 1991, 1 page, English Abstract Only.
Yoshihiro, et al, "Operating Cutter", Published JP63279843(A), Nov. 16, 1988, 1 page, Bibliographic Data Only, www.espacenet.com.
Susumu, "Operation Cutter", Published JP3037059(A), Feb. 18, 1991, 2 pages, Bibliographic Data Only, www.espacenet.com.

(Continued)

*Primary Examiner* — Corrine M McDermott
*Assistant Examiner* — Melissa Ryckman
(74) *Attorney, Agent, or Firm* — W. David Lee

(57) ABSTRACT

A microsurgical instrument including a cutting member and a base with an actuating mechanism that provides more efficient cutting of tissue.

4 Claims, 5 Drawing Sheets

OTHER PUBLICATIONS

Yoshihiro, "Operating Device", Published JP5154172(A), Jun. 22, 1993, 1 page, Bibliographic Data Only, www.espacenet.com.

Gordon, et al, "Anterior Capsulotomy Device and Procedure", Published JP2000503869(A), Apr. 4, 2000, 1 page, Bibliographic Data Only, www.espacenet.com.

Kiyoshi, "Surgical apparatus for a vitreous", JP2001087303, Apr. 3, 2001, 1 page, English Abstract Only, www.questel.com.

Yoshihiro, et al "cutter which is used for title surgery of device", Unexamined Utility Model JP63180026(U), Nov., 1988, 5 pages, Machine Translation.

* cited by examiner

MICROSURGICAL INSTRUMENT

FIELD OF THE INVENTION

The present invention generally pertains to microsurgical instruments. More particularly, but not by way of limitation, the present invention pertains to microsurgical instruments having a port for aspirating and cutting tissue.

DESCRIPTION OF THE RELATED ART

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. U.S. Pat. No. 4,577,629 (Martinez); U.S. Pat. No. 5,019,035 (Missirlian et al.); U.S. Pat. No. 4,909,249 (Akkas et al.); U.S. Pat. No. 5,176,628 (Charles et al.); U.S. Pat. No. 5,047,008 (de Juan et al.); U.S. Pat. No. 4,696,298 (Higgins et al.); and U.S. Pat. No. 5,733,297 (Wang) all disclose various types of vitrectomy probes, and each of these patents is incorporated herein in its entirety by reference.

Conventional vitrectomy probes include "guillotine style" probes and rotational probes. A guillotine style probe has an inner cutting member that reciprocates along its longitudinal axis. A rotational probe has an inner cutting member that reciprocates around its longitudinal axis. In both types of probes, the inner cutting members are actuated using various methods. For example, the inner cutting member can be moved from the open port position to the closed port position by pneumatic pressure against a piston or diaphragm assembly that overcomes a mechanical spring. Upon removal of the pneumatic pressure, the spring returns the inner cutting member from the closed port position to the open port position. As another example, the inner cutting member can be moved from the open port position to the closed port position using a first source of pneumatic pressure, and then can be moved from the closed port position to the open port position using a second source of pneumatic pressure. As a further example, the inner cutting member can be electromechanically actuated between the open and closed port positions using a conventional rotating electric motor or a solenoid. U.S. Pat. No. 4,577,629 provides an example of a guillotine style, pneumatic piston/mechanical spring actuated probe. U.S. Pat. Nos. 4,909,249 and 5,019,035 disclose guillotine style, pneumatic diaphragm/mechanical spring actuated probes. U.S. Pat. No. 5,176,628 shows a rotational dual pneumatic drive probe.

In many conventional vitrectomy probes, the cutting stroke of the inner cutting member is limited by contact with the closed, distal end of the probe at the end of the cutting stroke. Such actuation may dull the cutting surfaces of the probe. In many conventional vitrectomy probes, the return stroke of the inner cutting member is limited by the actuating piston or diaphragm contacting a stopping ring. This arrangement reduces the diaphragm area exposed to actuating pressure at the beginning of the cutting stroke. In conventional pneumatic piston (or diaphragm)/mechanical spring actuated probes, the use of a pre-loaded return spring requires relatively large actuating pressures to initiate the cutting stroke. Spring-returned probes also exhibit increasing spring return force as the cutting stroke progresses, which requires increased pneumatic pressure to complete the cutting stroke. This limitation is exacerbated in modern probes with higher cutting speeds because greater spring pre-load forces require correspondingly greater pneumatic actuation pressures.

Therefore, a need exists for an improved vitrectomy probe that exhibits more efficient cutting. Such efficiency should facilitate the minimization of the total air consumed during probe actuation, operation at lower pneumatic pressures, and operation at higher cutting speeds. Minimizing the total air consumed is particularly important for applications where pneumatic pressure is delivered via a pressurized tank that is periodically replaced. Operating at higher cutting speeds reduces the aspiration time between cuts and the turbulence of vitreous and retinal issues during cutting.

SUMMARY OF THE INVENTION

In one aspect, the present invention is a microsurgical instrument having a cutting member and a base. The cutting member has a tubular outer cutting member with a port for receiving tissue and a tubular inner cutting member disposed within the outer cutting member. The base has an actuating mechanism for reciprocating actuation of the inner cutting member so that the inner cutting member opens and closes the port and cuts tissue disposed in the port. The actuating mechanism includes a diaphragm chamber having a first wall portion and a second wall portion, a rigid center support disposed in the diaphragm chamber and having a first limiting surface and a second limiting surface, and a flexible diaphragm coupled to the center support and the base. Upon actuation of the inner cutting member, the first limiting surface contacts the first wall portion at an end of a cutting stroke of the inner cutting member, and the second limiting surface contacts the second wall portion at an end of a return stroke of the inner cutting member.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF PREFERRED EMBODIMENTS

Figure 1:
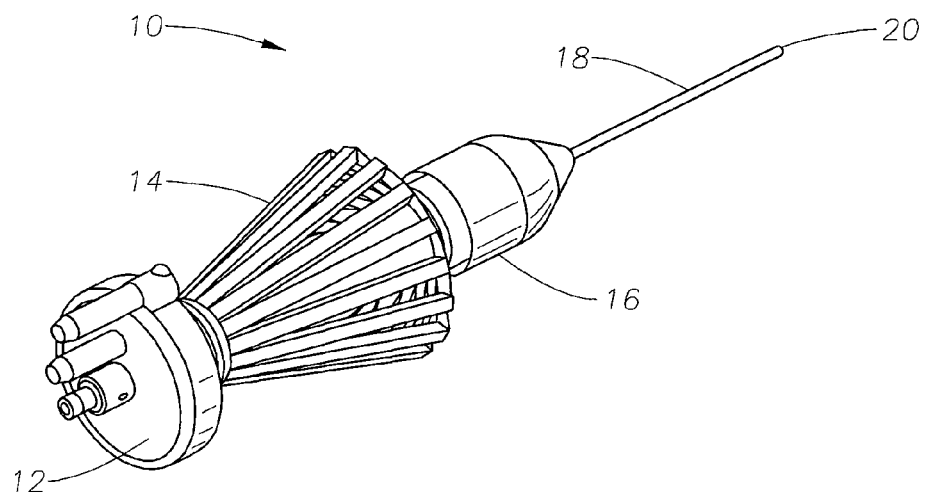
FIG. 1 is a perspective view of a microsurgical instrument according to a preferred embodiment of the present invention.

The preferred embodiments of the present invention and their advantages are best understood by referring to FIGS. 1 through 7 of the drawings, like numerals being used for like and corresponding parts of the various drawings.

Microsurgical instrument 10 preferably includes a base 12, an actuating handle 14, a nose member 16, and a cutting member 18 having a distal tip 20. As shown in the Figures, microsurgical instrument 10 is a vitrectomy probe. However, microsurgical instrument 10 may be any microsurgical cutting, aspiration, or infusion probe.

Base 12 includes an actuating mechanism 13 for actuating a tubular inner cutting member 110 of cutting member 18 in a reciprocating manner. Actuating mechanism 13 preferably includes a first pneumatic port 22, a second pneumatic port 24, a diaphragm chamber 26, a flexible diaphragm 28, and a rigid center support 30. Flexible diaphragm 28 is coupled to center support 30 and base 12. As shown in the Figures, flexible diaphragm 28 is frictionally coupled to both center support 30 and base 12. Alternatively, flexible diaphragm 28 may be frictionally coupled to base 12 and over-molded onto center support 30. Center support 30 has limiting surfaces 31a and 31b for interfacing with wall portions 33a and 33b of diaphragm chamber 26, respectively. Base 12 further includes an aspiration port 34 and a distal portion 12a having an aperture 12b and a distal tip 12c. A collar 36 couples distal portion 12a to actuating handle 14. Inner cutting member 110 is coupled to center support 30 and is slidably and fluidly coupled to base 12 via o-rings 38.

Actuating handle 14 preferably includes a proximal base 50, a distal base 52, and a plurality of flexible appendages 14a coupled to both base 50 and 52. Flexible appendages 14a may be made from any suitable springy material having a memory, such as titanium, stainless steel, or a suitable thermoplastic. Handle 14 surrounds distal portion 12a of base 12. Proximal base 50 is coupled to collar 36. Distal base 52 is received within a slidable collar 54. A user grasps microsurgical instrument 10 via handle 14. When a user exerts an inward pressure on flexible appendages 14a, flexible appendages 14a bend at or near 14b, straightening and elongating flexible appendages 14a, and moving collar 54 toward distal tip 20. When such pressure is removed, spring 55 returns flexible appendages 14a to the position shown in FIG. 2.

Nose member 16 preferably includes cam chamber 70 for receiving a cam member 72, a base chamber 74 for receiving distal tip 12c of base 12, a bushing 76 for receiving inner cutting member 110 of cutting member 18, and an outlet 78 for receiving a tubular outer cutting member 100 of cutting member 18. Cam member 72 is rotationally coupled to nose member 16 within aperture 12b of base 12 via dowel pins (not shown) inserted into each end of a bore 79. Cam member 72 preferably has a first stopping surface 80 for interfacing with collar 54, a second stopping surface 82 for interfacing with base 12, a clearance slot 84 for receiving inner cutting member 110 of cutting member 18, and a cam surface 86 for interfacing with bushing 76. An o-ring 88 slidably and fluidly seals nose member 16 to inner cutting member 110.

As described above, cutting member 18 preferably includes tubular outer cutter member 100 and tubular inner cutting member 110. Outer cutting member 100 has an inner bore 102, a closed end 104, a port 106 for receiving tissue, and cutting surfaces 108. Inner cutting member 110 has an inner bore 112, an open end 114, and a cutting surface 116.

In operation, vitrectomy probe 10 is operatively coupled to a microsurgical system 198. More specifically, pneumatic port 22 is fluidly coupled to a pneumatic pressure source 200 via a fluid line 202, pneumatic port 24 is fluidly coupled to a pneumatic pressure source 204 via fluid line 206, and aspiration port 34 is fluidly coupled to vacuum source 208 via fluid line 209. Inner bore 112 and fluid line 209 are primed with a surgical fluid. Microsurgical system 198 also has a microprocessor or computer 210, which is electrically coupled to pneumatic pressure sources 200 and 204 via interfaces 212 and 214, respectively.

Figure 6:
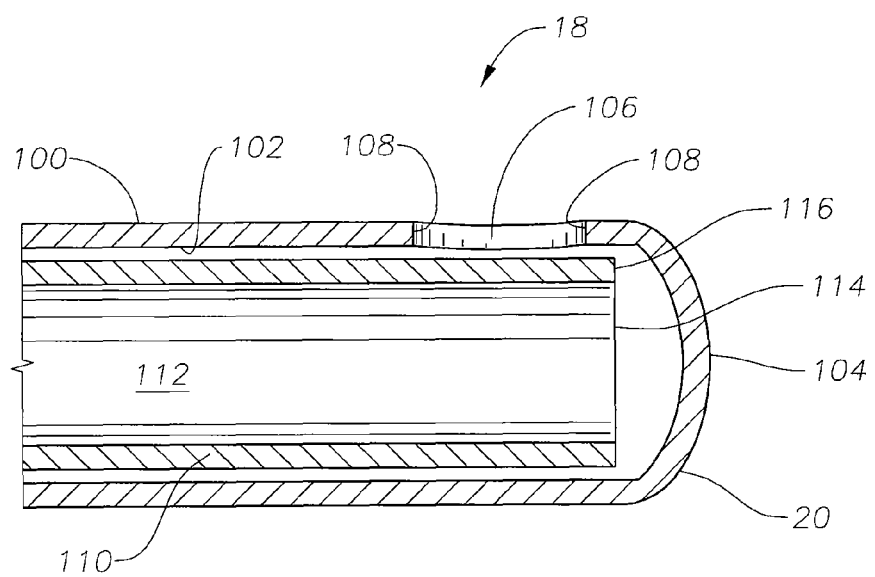
FIG. 6 is an enlarged, fragmentary, side, sectional view of the portion of the microsurgical instrument of FIG. 1 shown in circle 6 of FIG. 2.
Figure 2:
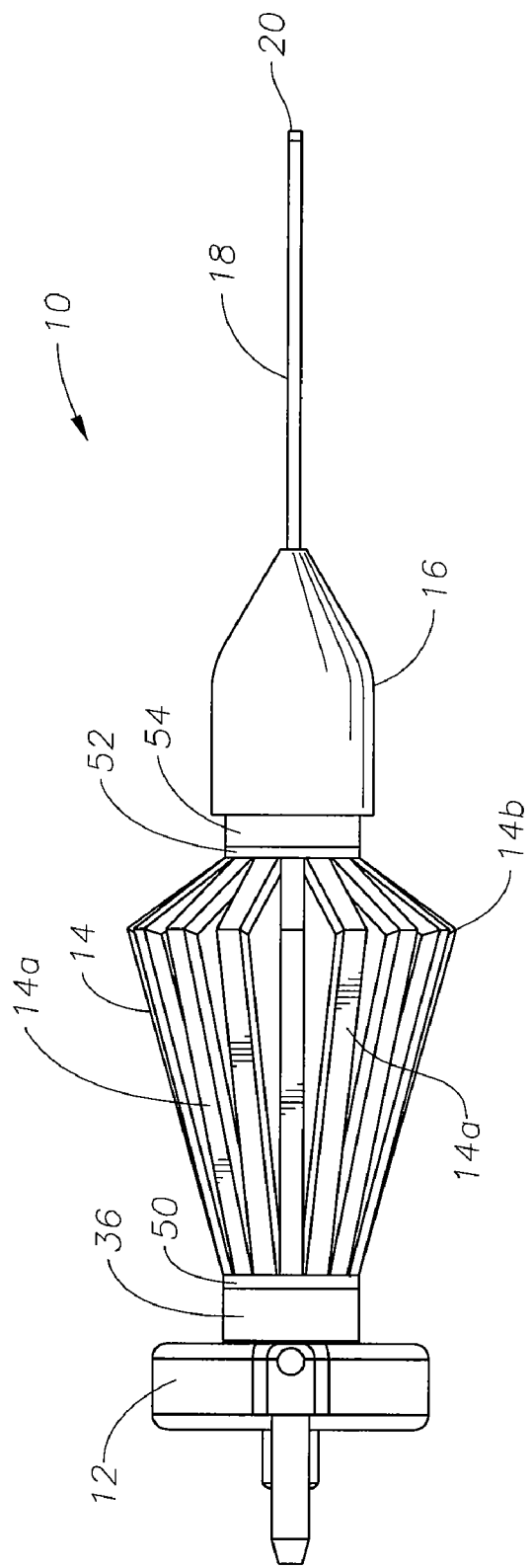
FIG. 2 is a top view of the microsurgical instrument of FIG. 1.
Figure 3:
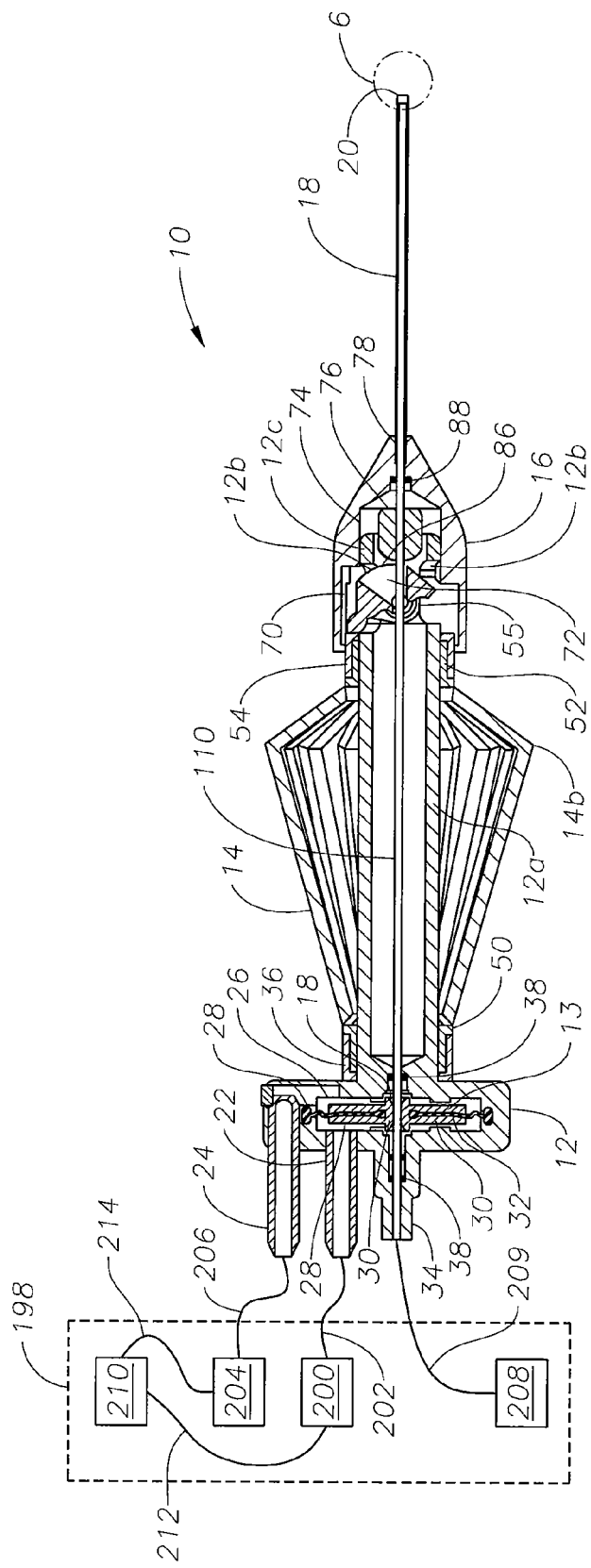
FIG. 3 is a side, sectional view of the microsurgical instrument of FIG. 1 shown operatively coupled to a microsurgical system.
Figure 4:
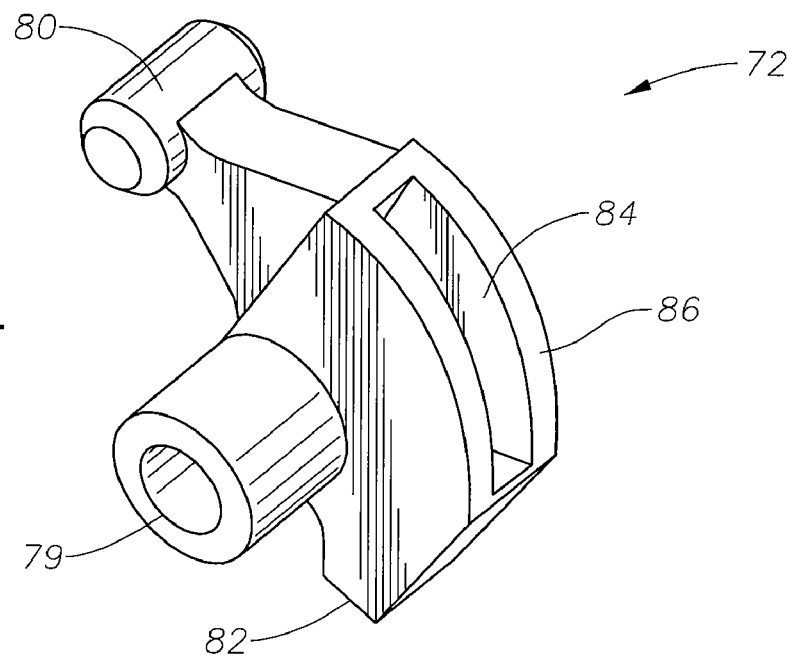
FIG. 4 is an enlarged, perspective view of the cam member of the microsurgical instrument of FIG. 1.
Figure 5:
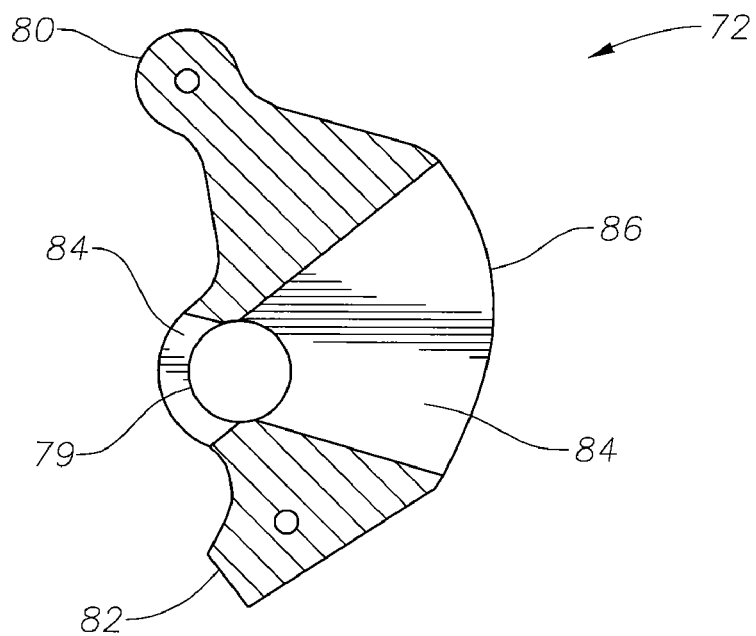
FIG. 5 is a cross-sectional view of the cam member of FIG. 4.
Figure 7:
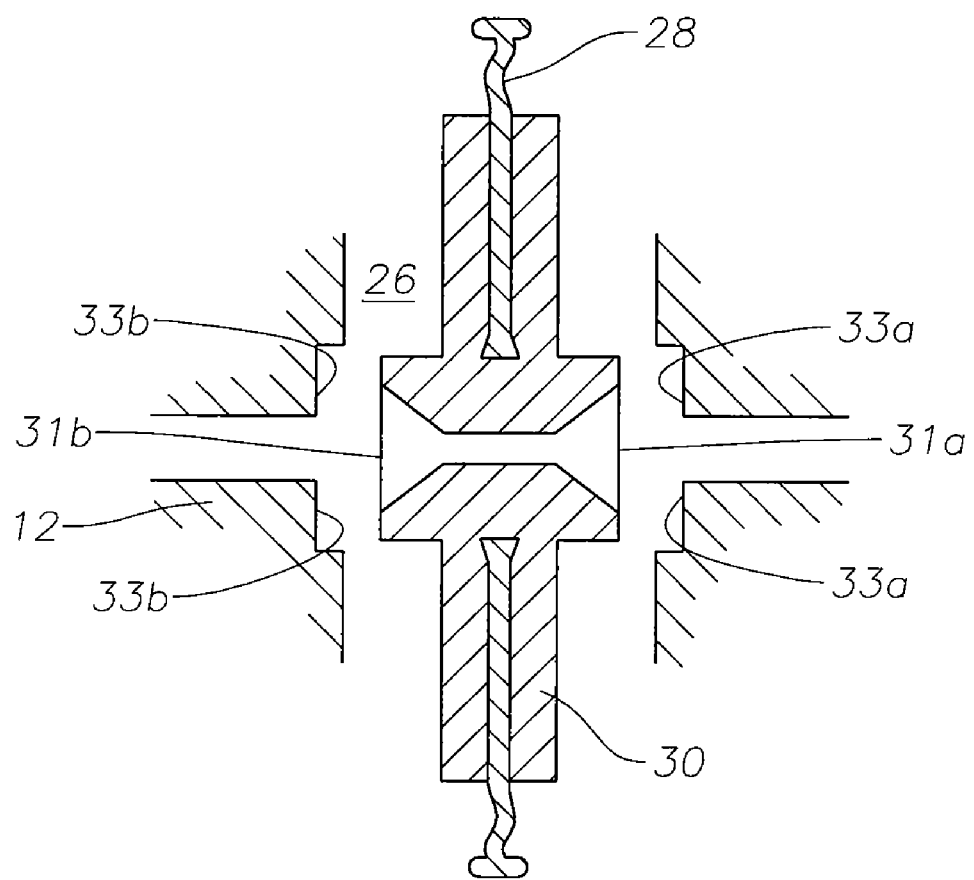
FIG. 7 is an enlarged, fragmentary, side, sectional view of a portion of the actuating mechanism of the microsurgical instrument of FIG. 1.

A surgeon inserts distal tip 20 into the posterior segment of the eye using a pars plana insertion. The surgeon selects a desired vacuum level for vacuum source 208. Tissue is aspirated into inner bore 112 via port 106. The surgeon selects a desired cut rate for probe 10 using microprocessor 210 and optionally a proportional control device (not shown), such as a foot controller. More specifically, microprocessor 210 uses pressurized gas sources 200 and 204 to create a cyclic pressure differential across diaphragm 28 so as to move center support 30, and thus inner cutting member 110, in a reciprocating manner at the desired cut rate. When the pressure provided to pneumatic port 22 is greater than the pressure provided to pneumatic port 24, inner cutting member 110 is moved toward distal tip 20 until open end 114 is past cutting surface 108, as shown in FIG. 6. This actuation closes port 106, allowing cutting surfaces 108 and 116 to cut the tissue within inner bore 112. The cut tissue is aspirated through inner bore 112, aspiration port 34, fluid line 209, and into a collection chamber (not shown). When the pressure provided to pneumatic port 24 is greater than the pressure provided to pneumatic port 22, inner cutting member 110 is moved away from distal tip 20, opening port 106 and allowing the further aspiration of tissue.

During actuation of inner cutting member 110, limiting surface 31a of center support 30 contacts wall portion 33a of diaphragm chamber 26 to precisely end the cutting stroke. Limiting surface 31b of center support 30 contacts wall portion 33b of diaphragm chamber 26 to precisely end the return stroke. When limiting surface 31a contacts wall portion 33a, cutting surface 116 of open end 114 of inner cutting member 110 is preferably disposed at or just past distal cutting surface 108 of outer cutting member 100. When limiting surface 31b contacts wall portion 33b, open end 114 is preferably disposed at or near proximal cutting surface 108 of outer cutting member 100. Such precision control of the actuation of inner cutting member 110 greatly increases the cutting efficiency of probe 10.

From the above, it may be appreciated that the present invention provides significant benefits over conventional vitrectomy probes. The present invention is illustrated herein by example, and various modifications may be made by a person of ordinary skill in the art. For example, although the present invention is described above in connection with a vitrectomy probe, it is equally applicable to aspiration probes, infusion probes, and other cutting probes.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A microsurgical instrument, comprising:
  a cutting member having:
    a tubular outer cutting member with a port for receiving tissue, said port having a distal cutting surface and a proximal cutting surface; and
    a tubular inner cutting member disposed within said outer cutting member and having a third cutting surface; and
  a base having an actuating mechanism for reciprocating actuation of said inner cutting member so that said inner cutting member opens and closes said port and cuts tissue disposed in said port, said actuating mechanism comprising:
    a diaphragm chamber having a distal wall portion and a proximal wall portion;
    a rigid center support disposed in said diaphragm chamber and having a rigid distal limiting surface and a rigid proximal limiting surface;
    a flexible diaphragm coupled to said center support and said base;
    a first pneumatic port for providing pressurized gas to a portion of said diaphragm chamber on a proximal side of said flexible diaphragm; and
    a second pneumatic port for providing pressurized gas to a portion of said diaphragm chamber on a distal side of said flexible diaphragm;
  whereby upon actuation of said inner cutting member via a pressure differential across said flexible diaphragm created using said first pneumatic port and said second pneumatic port, said rigid distal limiting surface contacts said distal wall portion when said third cutting surface is disposed proximate said distal cutting surface at an end of a cutting stroke in which said inner cutting member is moving in a distal direction, and said rigid proximal limiting surface contacts said proximal wall portion when said third cutting surface is disposed proximate said proximal cutting surface at an end of a return stroke in which said inner cutting member is moving in a proximal direction.

2. The microsurgical instrument of claim 1 wherein said instrument is a vitrectomy probe.

3. The microsurgical instrument of claim 1 wherein said diaphragm chamber, said center support, said flexible diaphragm, said first pneumatic port, and said second pneumatic port increase the cutting efficiency of said probe.

4. The microsurgical instrument of claim 1 wherein said rigid proximal limiting surface contacts said proximal wall portion when said third cutting surface is disposed at said proximal cutting surface at an end of a return stroke in which said inner cutting member is moving in a proximal direction.

* * * * *